United States Patent [19]

Preston et al.

[11] Patent Number: 5,776,489

[45] Date of Patent: Jul. 7, 1998

[54] CONTROLLED RELEASE CARBONIC ANHYDRASE INHIBITOR CONTAINING PHARMACEUTICAL COMPOSITIONS FROM SPHERICAL GRANULES IN CAPSULE ORAL DOSAGE UNIT FORM

[75] Inventors: Wendy Ann Preston, Suffern; Daniel Joseph Doyon, Florida, both of N.Y.; Stephen Patrick Simmons, Overland Park, Kans.

[73] Assignee: American Cyanamid Company, Madison, N.J.

[21] Appl. No.: 840,618

[22] Filed: Feb. 20, 1992

Related U.S. Application Data

[63] Continuation of Ser. No. 410,709, Sep. 21, 1989, abandoned.

[51] Int. Cl.[6] .................. A61K 9/58; A61K 9/62
[52] U.S. Cl. .................. 424/451; 424/457; 424/461; 424/462; 424/458; 424/490; 424/494; 424/495; 424/497; 424/499; 424/489
[58] Field of Search .................. 424/451, 458, 424/461, 462, 489, 494, 495, 497, 499; 514/363, 869

[56] References Cited

U.S. PATENT DOCUMENTS

| | | | |
|---|---|---|---|
| 2,554,816 | 5/1951 | Clapp et al. | 546/119 |
| 2,783,241 | 2/1957 | Young et al. | 540/139 |
| 2,980,679 | 4/1961 | Pala | 544/316 |
| 3,161,654 | 12/1964 | Shen | 548/500 |
| 4,029,776 | 6/1977 | Cafruny et al. | 424/240 |
| 4,173,626 | 11/1979 | Dempski et al. | 424/462 |
| 4,517,179 | 5/1985 | Raghunathan | 514/249 |
| 4,526,777 | 7/1985 | Blume et al. | 424/458 |
| 4,808,413 | 2/1989 | Joshi et al. | 424/499 |
| 4,837,030 | 6/1989 | Valorose, Jr. et al. | 424/494 |
| 4,844,909 | 7/1989 | Goldie et al. | 424/494 |
| 4,844,910 | 7/1989 | Leslie et al. | 424/495 |
| 4,867,985 | 9/1989 | Heafield et al. | 424/458 |
| 4,898,729 | 2/1990 | Miller et al. | 424/80 |

FOREIGN PATENT DOCUMENTS

2202143  9/1988  United Kingdom.

OTHER PUBLICATIONS

Physician's Desk Reference, 43rd Ed., Medical Economics Co. (1989), pp. 1116, 1117, 1137.

Avicel Microcrystalline Cellulose Spheres, FMC Corp. 1985.

Remington's Pharmaceutical Sciences, 1985, 17th Ed., Philadelphia, College of Pharmacy and Science, Chapter 68, Pharmaceutical Necessities, pp. 1278–1320.

Primary Examiner—Amy Hulina
Attorney, Agent, or Firm—Hedman, Gibson & Costigan, P.C.

[57] ABSTRACT

A controlled release pharmaceutical composition in oral dosage unit form comprising a hard or a soft shell capsule containing a filling comprising a therapeutically effective number of active spherical granules comprising an effective amount of at least one carbonic anhydrase inhibitor active medicament, a pharmaceutically acceptable normally solid diluent adapted to form a diffusable matrix for the carbonic anhydrase inhibitor active medicament and an optional pharmaceutically acceptable excipient. A method for the preparation and for the administration of the above defined composition is provided as well.

27 Claims, 6 Drawing Sheets

1

CONTROLLED RELEASE CARBONIC ANHYDRASE INHIBITOR CONTAINING PHARMACEUTICAL COMPOSITIONS FROM SPHERICAL GRANULES IN CAPSULE ORAL DOSAGE UNIT FORM

This application is a continuation of Ser. No. 07/410,709, filed Sep. 21, 1989, now abandoned.

FIELD OF THE INVENTION

The invention relates to controlled release pharmaceutical compositions in oral dosage units comprising hard or soft shell capsules filled with a therapeutically effective number of active spherical granules containing carbonic anhydrase inhibitor(s) as an active medicament, to a method for controlling the release of carbonic anhydrase inhibitor(s) in the blood stream of a warm-blooded mammal, and to a method for the preparation of the foregoing capsule oral dosage units.

The capsule oral dosage units provide excellent controlled release of the carbonic anhydrase inhibitor being delivered and uniform medicament dosage from capsule to capsule. They are effective at a broad range of dosages of carbonic anhydrase inhibitor active medicament including relatively low dosage ranges of carbonic anhydrase inhibitor active medicament.

BACKGROUND OF THE INVENTION

Carbonic anhydrase is an enzyme that catalyzes the reversible reaction of the hydration of carbon dioxide and the dehydration of carbonic acid. Carbonic anhydrase inhibitors have proven to be beneficial active medicaments in the treatment of various disease processes including simple (open-angle) glaucoma, secondary glaucoma, acute angle-closure glaucoma, particularly where it is desirable to delay surgery in order to lower intraocular pressure and certain convulsive disorders, e.g. epilepsy and mountain sickness. Certain carbonic anhydrase inhibitors are also effective in the promotion of diuresis in instances of abnormal fluid retention, e.g. cardiac edema. (*Physician's Desk Reference*, 43rd Edition, Medical Economics Company, 1989 (PDR 43rd Ed.)).

It is often important to control the release of a carbonic anhydrase inhibitor administered to a subject in order to achieve a slow release of the active medicament over a prolonged period of time extending the duration of the action of the medicament over that achieved by conventional delivery. However, most carbonic anhydrase inhibitors are slightly or sparingly soluble in water, i.e. aqueous solubility of less than about 20.0 mg/ml and therefore are difficult to formulate into controlled release dosage forms.

Diamox® (acetazolamide—Lederle Laboratories—Wayne, N.J.) has been formulated as sustained-release capsules filled with non-spherical granules of acetazolamide (U.S. Pat. Nos. 2,554,816, 2,980,679) in a wax matrix (PDR 43rd Ed.).

Dempski, et al., U.S. Pat. No. 4,173,626, disclose capsules comprising uncoated indomethacin (U.S. Pat. No. 3,161,654), pellets for immediate release, coated indomethacin pellets for prolonged release, and non-medicated pellets as volume fill. Indomethacin is a prostaglandin synthetase inhibitor.

The incorporation of water insoluble medicament containing active spheroids comprised of microcrystalline cellulose and at least one cellulose derivative into capsules, sachets, and cachets is disclosed in U.K. Patent Publication No. GB 2,202,143. None of the active medicaments are carbonic anhydrase inhibitors and sustained released is accomplished by the necessary inclusion of the cellulose dervative.

Valorose et al, U.S. Pat. No. 4,437,030, disclose hard gelatin or soft gelatin capsules filled with tetracycline compounds comprising active spherical granules. Tetracycline compounds are used primarily for their antimicrobial effects.

Concurrently, filed, copending application, Ser. No. 07/410,707, filed Sep. 21, 1989, now abandoned, discloses tablets comprising active spherical granules containing methazolamide (U.S. Pat. No. 2,783,241) and compressible spherical granules.

Concurrently filed, copending application, Ser. No. 07/410,706 filed Sep. 21, 1989, now abandoned discloses two pulse pharmaceutical delivery systems for 7-dimethyamino deoxy-6-demethyltetracycline or non-toxic acid addition salts thereof comprising initial loading components and pH sensitive polymer coated secondary loading components adapted to provide therapeutically effective blood concentrations of minocycline for up to about 24 hours in a once-a-day dosage.

FMC Corporation has disclosed the spheronization of 10 to 80 percent of anhydrous theophylline with 90 to 20 percent of microcrystalline cellulose and the spheronization of 10 percent of quinidine sulfate, chlorpheniramine maleate or hydrochlorothiazide with 90 percent of microcrystalline cellulose. (*Avicel® Microcrystalline Cellulose Spheres*, FMC Corporation, 1985). However, the hydrochlorothiazide containing spheres (hydrochlorothiazide aqueous solubility of 0.83 mg/ml) only released approximately 25 percent of the active medicament in 1 hour and took 4 hours to release approximately 50 percent of the active medicament when suspended in a rotating basket in 900 ml of distilled water.

Novel controlled release pharmaceutical compositions in capsule oral dosage unit form have now been discovered which provide suitable controlled release delivery of carbonic anhydrase inhibitor active medicament.

SUMMARY OF THE INVENTION

Figure 1:
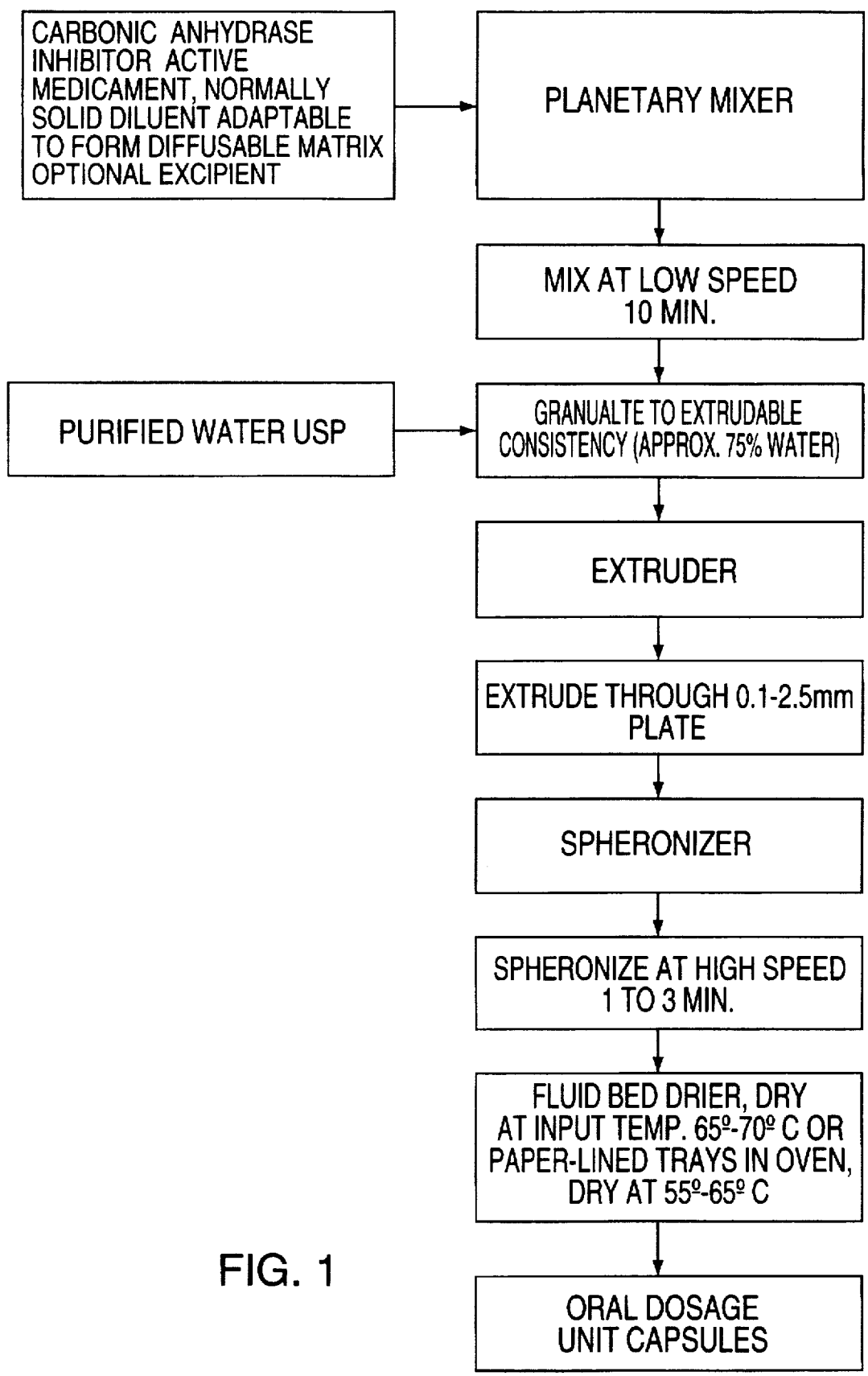
FIG. 1 is a graphic illustration of a method for production of capsules according to the present invention.

According to the present invention, there are provided controlled release pharmaceutical compositions in oral dosage unit form comprising a hard or a soft shell capsule containing a filling comprising (A) a therapeutically effective number of active spherical granules which comprise (i) an effective amount of at least one carbonic anhydrase inhibitor active medicament, (ii) a pharmaceutically acceptable normally solid diluent adapted to form a diffusable matrix for the carbonic anhydrase inhibitor active medicament, and optionally, (iii) at least one pharmaceutically acceptable excipient which may be the same as or different than (A)(ii).

The invention further contemplates oral dosage units in the form of capsules which contain two different types of active spherical granules (A-1) and (A-2) wherein (A-1) contains at least one carbonic anhydrase inhibitor active medicament and (A-2) contains at least one different active medicament.

The invention also provides a method for controlling the release of at least one carbonic anhydrase inhibitor active medicament in the blood stream of a warm-blooded mammal over a prolonged period of time comprising the ingestion of one or more oral dosage unit capsules as described above, as well as a method for the preparation of a controlled release pharmaceutical composition in oral dosage unit form comprising a hard or a soft shell capsule containing a filling comprising the steps of (a) blending (i) an effective amount of at least one carbonic anhydrase inhibitor active medicament, (ii) a pharmaceutically acceptable normally solid diluent adaptable to form a diffusable matrix for said at least one carbonic anhydrase inhibitor active medicament (a)(i), and optionally, (iii) at least one pharmaceutically acceptable excipient which may be the same as or different than (a)(ii); (b) granulating the resultant blend of step (a) in the presence of granulating liquid; (c) extruding the resultant granulate of step (b); (d) spheronizing the resultant extrudate of step (c) to form active spherical granules (A) derived from step (a); (e) drying active spherical granules (A); (f) at least partially filing a hard shell or a soft shell capsule with a therapeutically effective number of active spherical granuels (A); and optionally, (g) sealing the capsule.

The capsule unit dosage forms described above provide uniform carbonic anhydrase inhibitor active medicament content from capsule to capsule and are well adapted for formulation with and the administration of a wide range of dosages or amounts of carbonic anhydrase inhibitor active medicament including relatively low dosages and amounts. They provide a controlled release and a longer release of carbonic anhydrase inhibitor active medicaments which prolongs the effects of those active medicaments resulting in the administration of relatively low total amounts of the carbonic anhydrase inhibitor active medicament and less frequent administrations to a subject compared to conventional immediate release dosage forms. They avoid high local concentrations in a system which may cause side effects such as gastroirritability. They also are well adapted for the formulation of active spherical granule containing capsules wherein the active medicament has relatively low aqueous solubility (i.e. less than about 20.0 mg/ml).

DETAILED DESCRIPTION OF THE INVENTION

A novel controlled release pharmaceutical composition in oral dosage unit form has been discovered comprising a hard or a soft shell capsule containing a filling comprising a therapeutically effective number of active spherical granules. Many benefits can be realized from this novel oral dosage unit form over other conventional controlled release unit dosage forms. For example, the controlled release capsules of the present invention can deliver a variety of carbonic anhydrase inhibitor active medicaments in a wide range of dosages including relatively low dosages, are easy to manufacture, have great uniformity from capsule to capsule, and are easy to swallow. Additionally, different active medicaments and other fillers can be combined with relative ease in the capsule. The capsules containing the active spherical granules provide a superiorly controlled delivery of carbonic anhydrase inhibitor active medicament to a subject which results in the ability of the carbonic anhydrase inhibitor active medicament in the oral dosage unit form to sustain a desired blood level in a subject for a relatively long period of time. Therefore, less frequent administration of the carbonic anhydrase inhibitor active medicament to a subject and better subject compliance with a medicament regimen is possible.

The present invention is widely applicable to a number of carbonic anhydrase inhibitor active medicaments, particularly those with relatively low solubility in water. Multiple active medicaments can be delivered in a single oral unit dosage form as well.

Further advantages of the invention are achieved by processing onto the active spherical granules, one or more film coatings which can further modify the properties of the granules, and therefore of the capsules, such as release rates, disintegration rates, color, physical appearance and the like.

Oral dosage unit forms are those which are orally administered and contain carbonic anhydrase inhibitor active medicaments which are absorbed into the blood stream from the alimentary tract.

A therapeutically effective number of active spherical granules is that number which delivers and maintains a recommended dosage or concentration level of a particular carbonic anhydrase inhibitor active medicament to the blood stream or plasma of a subject within a recommended period of time and maintains that level for a further recommended period of time. Such an amount will depend upon the carbonic anhydrase inhibitor active medicament prescribed and the age, weight, sex, sensitivity and the like of the individual subject.

Although several carbonic anhydrase inhibitor active medicaments are suitable for use in the present invention, the preferred carbonic anhydrase inhibitor active medicament is methazolamide. U.S. Pat. No. 2,783,241, which is useful in the treatment of chronic simple glaucoma and secondary glaucoma, and is prescribed preoperatively in acute angle closure glaucoma where the delay of surgery is desired in order to lower intraoccular pressure. Methazolamide has an aqueous solubility at 25° C. of 1.5 mg/ml, and its solubility increases at higher pH, e.g. 3.4 mg/ml in pH 7.2 phosphate buffer. It is presently available under the tradename Neptazane® from Lederle Laboratories (PDR 43rd Ed.), and it is typically administered in dosages of about 50 mg to about 100 mg two to three times daily for a normal adult human being. Oral dosage units typically comprise from about 25 mg to about 75 mg of methazolamide.

Preferably, the unit dosage forms of the present invention will release not more than about 50 percent of the methazolamide from the active spherical granules in about 1 hour and not less than about 75 percent of the methazolamide from the active spherical granules in about 12 hours when suspended in pH 4.5 acetate buffer at about 37° C. at a methazolamide concentration of about 50 mg of methazolamide/900 ml of buffer.

The normally solid diluent adapted to form a diffusable matrix for the carbonic anhydrase inhibitor active medicament preferably comprises microcrystalline cellulose. Suitable forms of microcrystalline cellulose are, for example, the materials sold as Avicel®-PH-101 and Avicel®-PH-105 (available from FMC Corporation, American Viscose Division, Avicel Sales, Marcus Hook, Pa., U.S.A.). Avicel®-PH-101 is characterized as having an average particle size of 50 um, particle size specification of +60 mesh less than 1 percent and +200 mesh less than or equal to 30.0 percent, moisture specification of less than 5.0 percent and acceptable flow properties.

Avicel®-PH-105 is characterized as having an average particle size of 20 um, particle size specification of +400 mesh less than or equal to 1.0 percent, moisture specification of less than 5.0 percent, and poor flow properties.

The crystalline structure of micro-crystalline cellulose is relaxed when combined with excessive or large amounts of water, i.e., greater than about 30 percent by weight of microcrystalline cellulose and water combined, preferably greater than about 50 percent, and most preferably about 75 percent, losing most or all disintegration properties it possessed and forming a diffusable matrix. This normally solid diluent adapted to form a diffusable matrix can also comprise a mixture of microcrystalline cellulose and sodium carboxymethyl cellulose such as the material sold as Avicel®RC-581 by FMC Corporation. The choice of normally solid diluent adapted to form a diffusable matrix can be manipulated to achieve the desired release rate of the active medicament.

Release rates can also be controlled by the proper selection of excipients in the active spherical granules or in the capsules. Such excipients include lactose, other monoor di-saccharides, microcrystalline cellulose, polyvinylpyrrolidone, hydroxypropylmethyl cellulose, microcrystalline cellulose and lactose, microcrystalline cellulose and sodium carboxymethyl cellulose, mixtures of any of the foregoing and the like as well as others with which those skilled in this art will be familiar, most of which are listed in standard references, for example, *Remington's Pharmaceutical Sciences*, 1985, 17th Edition, Philadelphia College of Pharmacy and Science, Chapter 68, Pharmaceutical Necessities, pages 1278–1320.

Excipients such as mono- or di-saccharides may also be formed into non-pareil seeds which may be used in addition to the active spherical granules as an independent filler for the capsules. Such seeds are generally about 0.1 to about 2.0 mm in size and typically are about 1.0 millimeter in size and comprise, for example, a blend of sugar and starch.

The non-pareil seeds can also be coated with an effective amount of at least one active medicament which may be the same as or different than that found in the active spherical granules.

The active spherical granules of the present invention preferably have an average diameter in the range of from about 0.1 to about 2.5 millimeters. Most preferably, the active spherical granules have an average diameter in the range of from about 0.8 to about 1.2 millimeters.

In a preferred feature of the present invention, the active spherical granules and/or any non-pareil seeds, may include a layer or film of a polymer coating which is substantially uniform. Most preferably, this layer or film will comprise a top layer of the same or a different polymer over an intermediate polymer layer.

The film forming polymer, if used, can vary widely in type and amount which correlates to film thickness. This type of polymer should be selected in accordance with the carbonic anhydrase inhibitor active medicament incorporated into the oral dosage unit form.

Although from about 1 to less than about 25 weight percent of film content based on the weight of the film coated granules is suitable for most readily gastric juice erodable polymers, it is preferred to use about 1 to about 5 percent of any film.

Illustrative but not limiting film forming polymers are cellulose and acrylic acid based polymers. Particularly to be mentioned are methyl cellulose, ethyl cellulose, hydroxyethyl cellulose, hydroxypropyl cellulose, hydroxypropyl methyl cellulose, hydroxypropyl methyl cellulose phthalate, cellulose acetate phthalate, hydroxypropyl methylcellulose succinate, polymers and copolymers of (meth)acrylic acid and (meth)acrylic acid methyl ester, and mixtures of any of the foregoing. The coatings can include conventional additives, such as plasticizers, pigments, colorants, etc. The plasticizers can include mineral oil, high boiling esters, vegetable oils and the like. Commercial coating compositions found to be useful include Eudragit® a product of Rohm Pharma, Weiterstadt, Germany and Surelease®, a product of Colorcon, Inc., West Point, Pa. The former comprises an anionic polymerizate of methacrylic acid and methyl methacrylate. The latter comprises an aqueous dispersion of ethyl cellulose, dibutyl sebacate, oleic acid, fumed silca, and ammonium hydroxide.

Preferred as coating materials are ethyl-cellulose and hydroxypropyl methylcellulose.

A suitable form of ethylcellulose is one having a viscosity in the range of 5 to 100 cps at 20° C. (U.S. National Formulary XIII)(content of ethoxy groups 44 to 51 percent by weight), and more particularly a viscosity of 50 cps at 20° C. (content of ethoxy groups 48 to 49 percent by weight). A suitable form of hydroxy- propyl methylcellulose is one having a viscosity in the range 3 to 100 cps at 20° C., (U.S. National Formulary XIII), and more particularly a viscosity of 6 cps at 20° C.

The spherical granules can, if desired, be coated with an aqueous or organic solvent solution of the desired film forming polymer, using fluid bed technology or pan-coating, and the like, but preferably fluid beds are used.

For best results, if a film coating is used, a 1 percent weight gain level precoat and overcoat of hydroxypropyl methylcellulose are preferred in addition to the standard coating when using aqueous formulations.

The amounts of components (A)(i), (A)(ii) and (A)(iii) which comprise the active spherical granules (A) can vary broadly but will usually be in the range of from about 10 to about 90 parts by weight of (A)(i), from about 90 to about 10 parts by weight of (A)(ii), and from zero to about 75 parts by weight of (A)(iii) based upon 100 parts by weight of active spherical granules (A). Preferably, the active spherical granules comprise either from about 10 to about 75 parts by weight of (A)(i), and from about 90 to about 25 parts by weight of (A)(ii) based upon 100 parts by weight of (A) or from about 10 to about 80 parts by weight of (A)(i), from about 75 to about 10 parts by weight of (A)(ii), and from about 10 to about 75 parts by weight of (A)(iii) based upon 100 parts by weight of (A). Most preferably, (A)(i) comprises about 50 parts by weight by weight and (A)(ii) comprises about 50 parts by weight based upon 100 parts by weight of (A) or (A)(i) comprises from about 10 to about 50 parts by weight, (A)(ii) comprises from about 25 to about 65 parts by weight, and (A)(iii) comprises from about 10 to about 50 parts by weight based upon 100 parts by weight of (A). Special mention is made where (A) comprises about 25 parts by weight of (A)(i), from about 25 to about 65 parts by weight of (A)(ii) and from about 10 to about 50 parts by weight of (A)(iii) based-upon 100 parts by weight of (A).

The therapeutically effective amount of active spherical granules used to fill a capsule of the present invention can comprise a mixture of two or more independently therapeutically effective amounts of two or more different active spherical granules provided that at least one of the active spherical granules contains a carbonic anhydrase inhibitor active medicament.

The hard shell capsules used in the present invention are generally comprised of gelatin, water, and optionally, FD&C colorants, opacifying agents such as titanium oxide, sulfur dioxide to prevent decomposition during manufacturing or a combination of any of the foregoing. They generally comprise two sections, one slipping over the other, completely surrounding the filling.

The soft shell capsules used in the present invention are generally a soft, globular, gelatin shell somewhat thicker than the shell of the hard shell capsules. The gelatin is usually plasticized by the addition of glycerin, sorbitol or a similar polyol. They may also contain a preservative to prevent the growth of fungi.

The capsules can be formed and filled by any conventional capsule forming and/or filling machine and optionally may be sealed by any means commonly known to one of ordinary skill in the pharmaceutical arts including but not limited to spot-welding, gelatin bands and matched locking rings.

FIG. 1 illustrates the typical steps in the preparation of the oral unit dosage forms of the present invention. Firstly, in step (a), an effective amount of at least one carbonic anhydrase inhibitor active medicament (i), a pharmaceutically acceptable normally solid diluent adaptable to form a diffusable matrix for the at least one carbonic anhydrase inhibitor active medicament (ii), and optionally, at least one pharmaceutically acceptable excipient which may be the same as or different than (a)(ii), (iii), is blended in a mixer, e.g. a Hobart mixer. The resultant blend of step (a) is granulated with a granulating liquid, e.g. an aqueous solution or an organic solvent and preferably water, until the proper consistency, e.g. greater than about 30 percent water, preferably greater than 50 percent water, and most preferably 75 percent water to provide extensive wetting of the blend of step (a), for extrusion is realized. The resultant granulated mass is then extruded through a suitably sized, e.g. 1.0 mm, perforated plate and is spheronized at high speed for a time sufficient to form spherical granules, e.g. one to three minutes. Active spherical granules (A) are formed from the spheronization of the extrudate derived from step (a). The wet spherical granules are then dried in conventional equipment at suitable temperatures, e.g. such as tray driers at 55 to 65° C. or a conventional fluidized bed dryer system at 65 to 70° C. to a low moisture level, e.g. about 2.5 to about 5 percent. The active spherical granules may then, optionally, be coated as explained above. A hard or soft shell capsule is then at least partially filled with a therapeutically effective number of active spherical granules (A) by conventional means known to one of ordinary skill in the pharmaceutical arts. The capsule may then, optionally, be sealed by conventional means known to one of ordinary skill in the pharmaceutical arts as well.

The oral dosage unit forms described above may release the carbonic anhydrase inhibitor active medicament(s) into the blood stream of a warm-blooded mammal after ingestion.

The oral dosage unit forms of the present invention may also optionally include additional active medicament(s) which are the same as or different than (A)(i), lubricants, disintegrants which are the same as or different than (A)(ii), plasticizers, colorants, pigments, flavorings, additional excipients which may be the same as or different than (A)(ii) or (A)(iii), or a combination of any of the foregoing.

DESCRIPTION OF THE PREFERRED EMBODIMENTS

The following examples illustrate the invention without limitation. All parts are given by weight unless otherwise indicated.

EXAMPLE 1

A blend is prepared by mixing 50 parts of carbonic anhydrase inhibitor active medicament, methazolamide (Neptazane®—Lederle Laboratories), and 50 parts of normally solid diluent adaptable to form a diffusable matrix for the carbonic anhydrase inhibitor active medicament, microcrystalline cellulose (Avicel®—PH-101—FMC Corp.), in a planetary mixer for 10 minutes. The blend is then granulated to an extrudable consistency with the addition of water, and the resultant granulate is extruded through a 1.0 mm plate. The resultant extrudate is spheronized at high speed for one to three minutes. The resultant spherical granules are dried in a fluid bed dryer at 65° C. to 70° C. until the moisture content is about 2.54 percent, to form active spherical granules.

Figure 2:
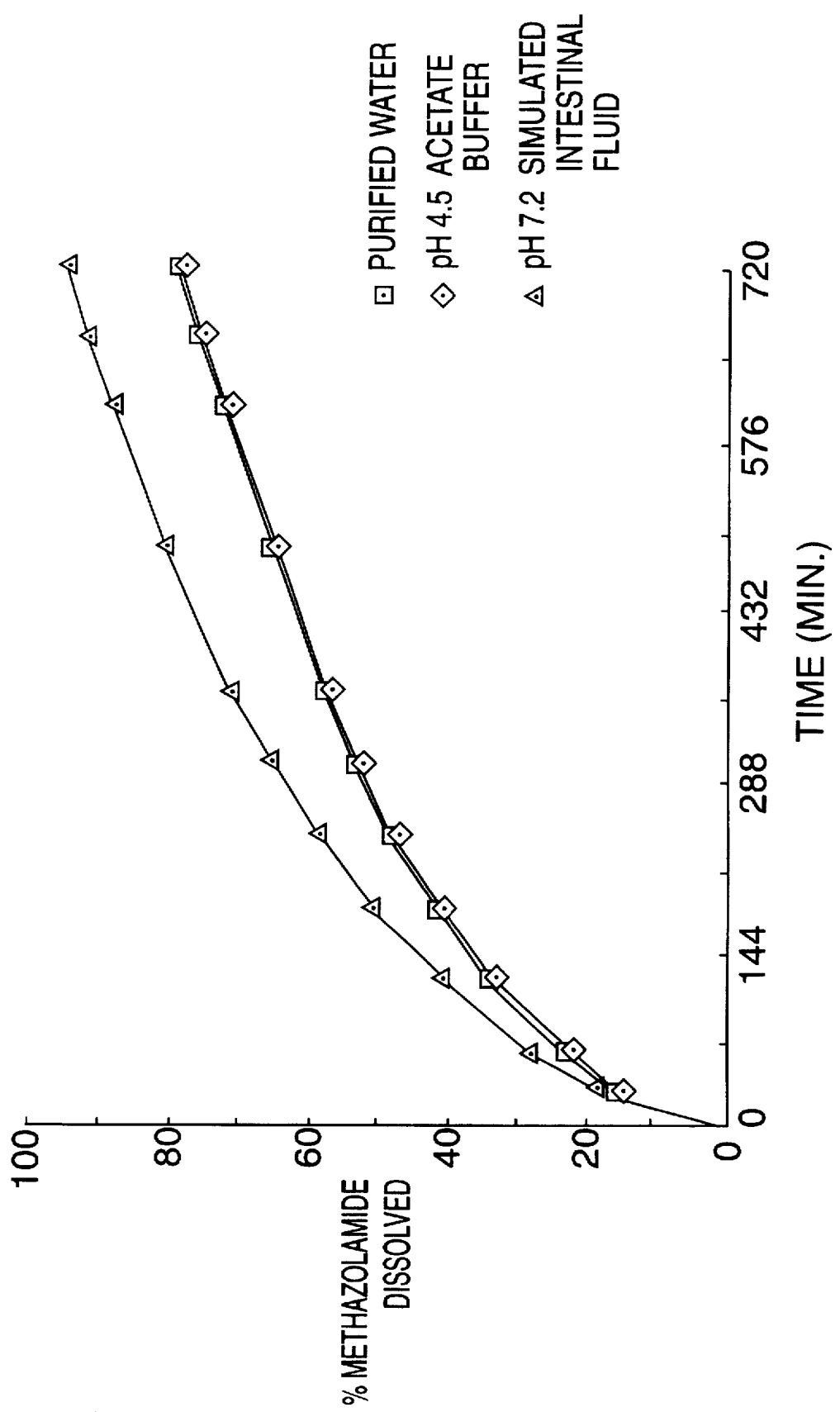
FIG. 2 is a graphic illustration of the release rate of carbonic anhydrase inhibitor active medicament from active spherical granules of the present invention in various media.

The carbonic anhydrase inhibitor active medicament release rate of the active spherical granules is determined by U.S.P. XXI test methods stirring with paddles in each of a medium with a pH of 4.5 and an acetate buffer, purified water, and simulated intestinal fluid with a pH of 7.2. The results are summarized in Table 1 and appear in FIG. 2 in graph form.

TABLE I

Release Rate of Carbonic Anhydrase Inhibitor Active Medicament[A] From Active Spherical Granules

| Time Minutes | Percent Released[B] Acetate Buffer pH 4.5 | Percent Released[C] Purified Water | Percent Released[D] Simulated Intestinal Fluid pH 7.2 |
| --- | --- | --- | --- |
| 30 | 14.8 ± 0.8 | 15.6 ± 0.9 | 18.1 ± 1.5 |
| 60 | 22.6 ± 0.5 | 23.2 ± 1.0 | 27.7 ± 1.6 |
| 120 | 33.3 ± 0.5 | 33.8 ± 0.9 | 40.9 ± 1.8 |
| 180 | 41.3 ± 0.4 | 41.8 ± 0.9 | 50.9 ± 1.9 |
| 240 | 47.6 ± 0.5 | 48.1 ± 0.8 | 58.8 ± 1.9 |
| 300 | 53.0 ± 0.6 | 53.4 ± 0.8 | 65.6 ± 1.8 |
| 360 | 57.8 ± 0.5 | 58.1 ± 0.8 | 71.3 ± 2.0 |
| 480 | 65.5 ± 0.4 | 66.0 ± 0.8 | 80.7 ± 2.0 |
| 600 | 72.2 ± 0.5 | 72.9 ± 0.9 | 88.3 ± 2.2 |
| 660 | 75.5 ± 0.5 | 76.2 ± 0.7 | 91.7 ± 2.0 |
| 720 | 78.2 ± 0.5 | 79.1 ± 0.8 | 94.7 ± 2.1 |

A—Methazolamide - Neptazane ® - Lederle Laboratories.
B—U.S.P. XXI test method; medium pH 4.5 with acetate buffer; stirred with paddles.
C—U.S.P. XXI test method; purified water; stirred with paddles.
D—U.S.P. XXI test method; simulated intestinal fluid pH 7.2; stirred with paddles.

Example 1 illustrates that in a medium of pH 4.5 and acetate buffer, in purified water, and in simulated intestinal fluid pH 7.2, not more than about 28 percent of the methazolamide is released in about one hour, and in a medium of pH 4.5 and acetate buffer and in purified water not less than about 78 percent of the methazolamide is released in about twelve hours. In simulated intestinal fluid pH 7.2, about 94 percent is released in a 12 hour period.

This demonstrates that carbonic anhydrase inhibitor active medicament containing active spherical granules of the present invention and therefore hard or soft shell capsules filled with those active spherical granules provide excellent controlled release properties over twelve hours.

EXAMPLE 2

Active spherical granules are prepared by the method of Example 1 and divided into three portions.

Figure 3:
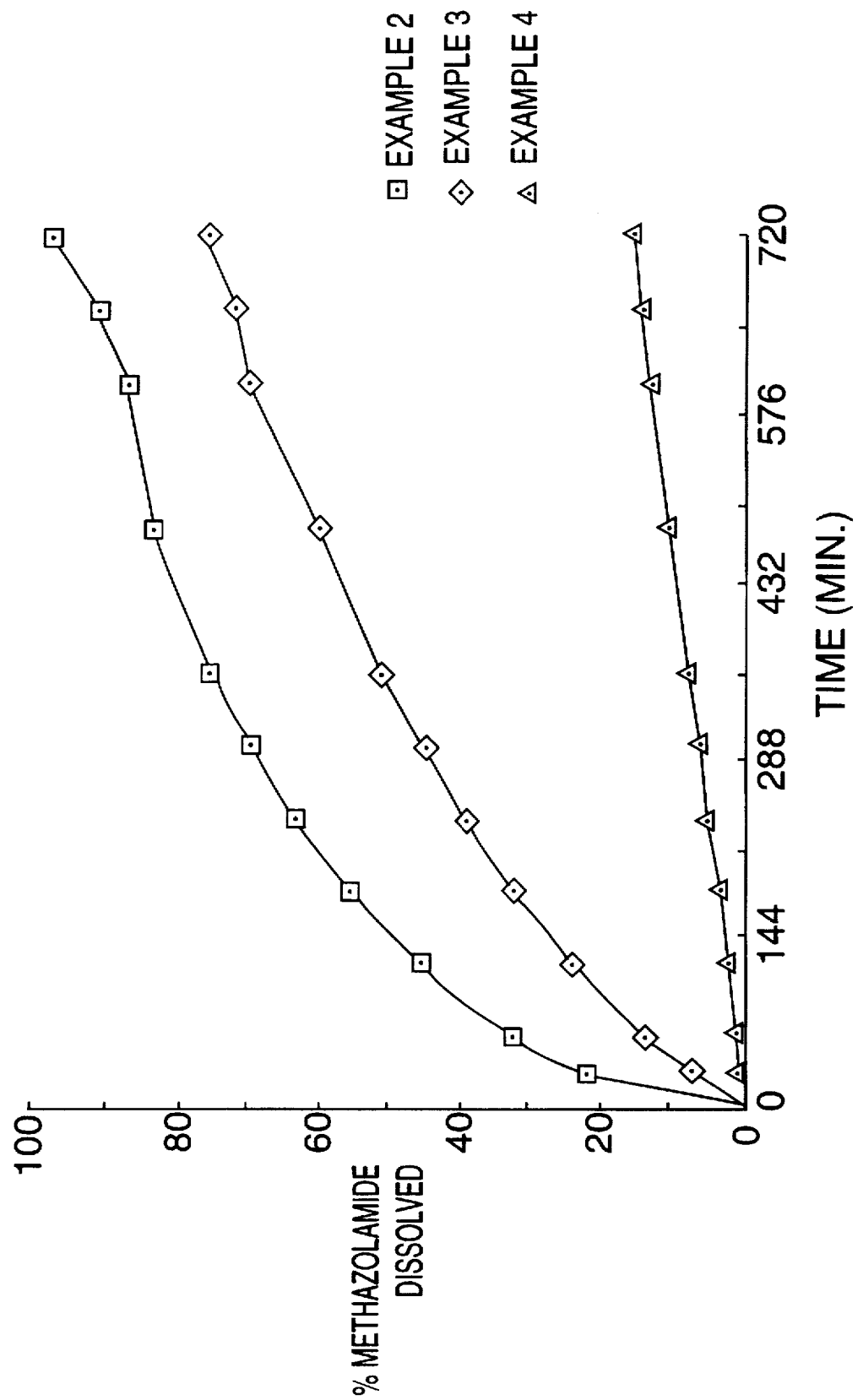
FIG. 3 is a graphic illustration of the effect of coatings on the release rate of carbonic anhydrase inhibitor active medicament from active spherical granules of the present invention.

The carbonic anhydrase inhibitor active medicament (methazolamide—Neptazane®—Lederle Laboratories) release rate of the first portion of active spherical granules is determined by U.S.P. XXI test methods stirring with paddles in simulated intestinal fluid, and in purified water. An attempt is made to determine the release rate in gastric fluid with a pH of 1.2, but sink conditions could not be maintained due to the poor solubility and the degradation of methazolamide in that medium. The results are summarized in Table II. The results in simulated intestinal fluid appear in FIG. 3 in graph form.

EXAMPLE 3

The active spherical granules of the second portion prepared in Example 2 are coated with 1 percent by weight of the active spherical granules in that portion of a polymer coating (aqueous dispersion of ethyl cellulose, dibutyl sebacate, oleic acid, fumed silica, and ammonium hydroxide—Surelease®—Colorcon, Inc.—West Point, Pa.).

The carbonic anhydrase inhibitor active medicament (methazolamide—Neptazane®—Lederle Laboratories) release rate of this coated second portion of active spherical granules is determined by U.S.P. XXI test methods stirring with paddles in simulated intestinal fluid and in purified water. An attempt is made to determine the release rate in gastric fluid with a pH of 1.2, but sink conditions could not be maintained due to the poor solubility and the degradation of methazolamide in that medium. The results are summarized in Table II. The results in simulated intestinal fluid appear in FIG. 3 in graph form.

EXAMPLE 4

The active spherical granules of the third portion prepared in Example 2 are coated with 5 percent by weight of the active spherical granules in that portion of a polymer coating (aqueous dispersion of ethyl cellulose, dibutyl sebacate, oleic acid, fumed silica, and ammonium hydroxide—Surelease®—Colorcon, Inc.—West Point, Pa.).

The carbonic anhydrase inhibitor active medicament (methazolamide—Neptazane®—Lederle Laboratories) release rate of this coated third portion of active spherical granules is determined by U.S.P. XXI test methods stirring with paddles in simulated intestinal fluid and in purified water. An attempt is made to determine the release rate in gastric fluid with a pH of 1.2, but sink conditions could not be maintained due to the poor solubility and the degradation of methazolamide in that medium. The results are summarized in Table II. The results in simulated intestinal fluid appear in FIG. 3 in graph form.

TABLE II

Effects of Coatings on Carbonic Anhydrase Inhibitor Active Medicament[A] Release Rates from Active Spherical Granules

| | Example | | |
|---|---|---|---|
| | 2 (Uncoated) Percent Released[B] | 3 (1% w/w Coating) Percent Released[B] | 4 (5% w/w Coating) Percent Released[B] |
| Medium-Simulated Intestinal Fluid (pH 7.2) Time (mins) | | | |
| 60 | 31.55 ± 0.49 | 14.2 ± 0.28 | 1.55 ± 0.21 |
| 120 | 44.30 ± 0.71 | 23.9 ± 0.42 | 2.70 ± 0.28 |
| 240 | 62.45 ± 0.07 | 39.1 ± 0.71 | 5.2 ± 0.57 |
| 360 | 74.55 ± 0.64 | 50.7 ± 0.71 | 7.6 ± 0.85 |
| 480 | 82.25 ± 0.64 | 59.8 ± 1.41 | 9.7 ± 0.99 |
| 600 | 87.70 ± 3.82 | 68.4 ± 0.0 | 11.9 ± 1.13 |
| 720 | 93.30 ± 0.99 | 75.55 ± 2.05 | 14.0 ± 1.20 |
| Medium-Acetate Buffer (pH 4.5) Time (mins) | | | |
| 60 | 22.50 ± 3.25 | 11.7 ± 0.14 | 2.30 + 0.14 |
| 120 | 34.00 ± 1.98 | 18.95 ± 0.35 | 3.25 ± 0.21 |
| 240 | 47.95 ± 1.63 | 30.05 ± 0.21 | 5.05 ± 0.21 |
| 360 | 57.75 ± 1.48 | 39.0 ± 0.14 | 6.65 ± 0.21 |
| 480 | 65.35 ± 1.77 | 46.4 ± 0.28 | 8.20 ± 0.28 |
| 600 | 71.95 ± 1.77 | 53.2 ± 0.28 | 9.55 ± 0.21 |
| 720 | 78.05 ± 1.77 | 59.45 ± 0.45 | 10.70 ± 0.28 |

A—methazolamide - Neptazane ® - Lederle Laboratories
B—U.S.P. XXI test method; stirred with paddles.

Examples 3 and 4 when compared with Example 2 demonstrate that release rates of carbonic anhydrase inhibitor active medicament from active spherical granules can be further altered by the application of polymer coatings to the active spherical granules.

Example 2 is essentially a repeat of Example 1 and the data from both Examples appear to be consistent as any variations of release rate fall well within experimental error.

EXAMPLE 5

The procedure of Example 1 is followed substituting 1.2 to 1.8 mm plates for the extruder plates.

Figure 4:
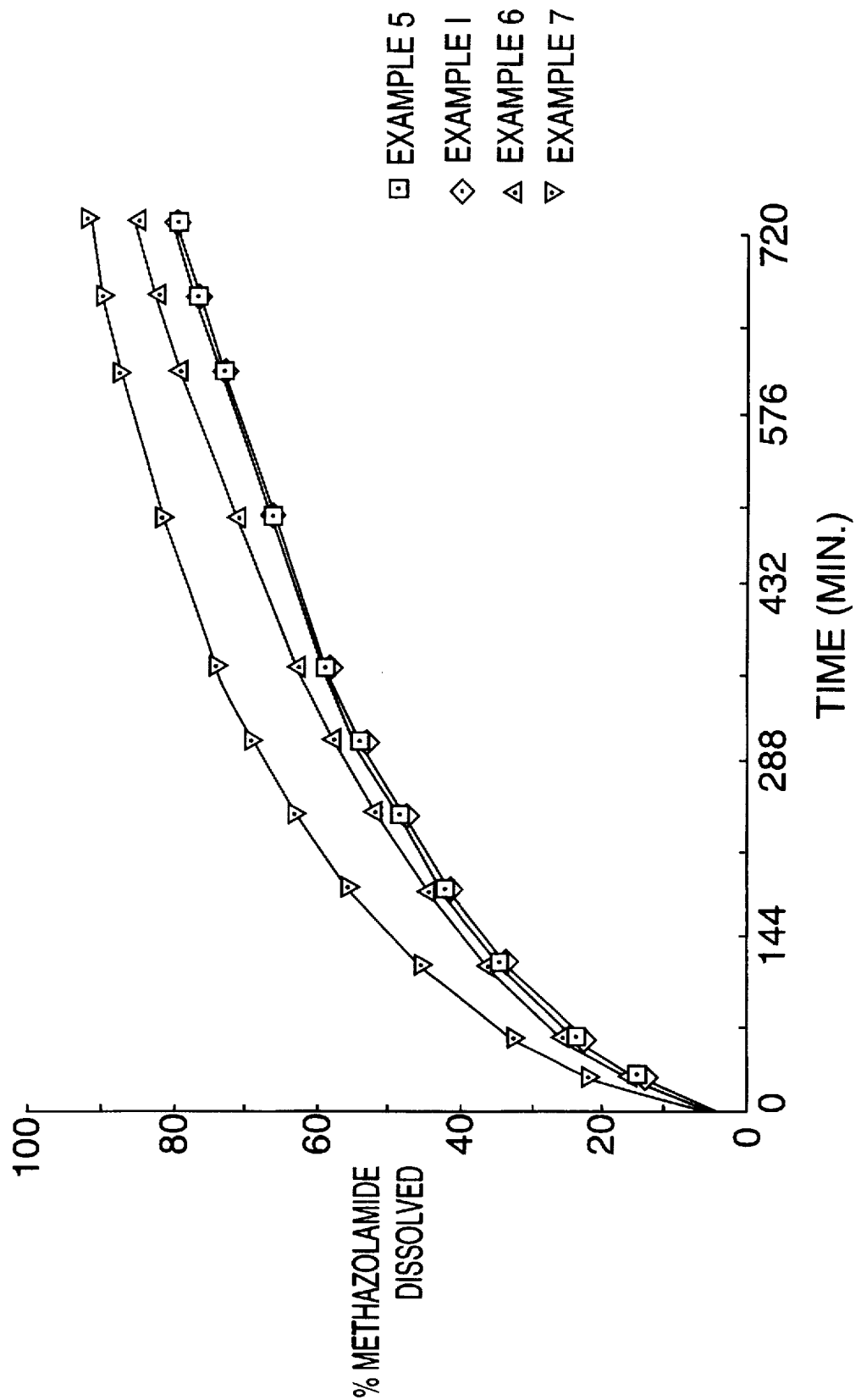
FIG. 4 is a graphic illustration of the effect of spherical granule size on the release rate of carbonic anhydrase inhibitor active medicament from active spherical granules of the present invention.

The carbonic anhydrase inhibitor active medicament release rate of the active spherical granules is determined by U.S.P. XXI test methods stirring with paddles in a medium with a pH of 4.5 and an acetate buffer. The results are summarized in Table III and appear in FIG. 4 in graph form.

EXAMPLE 6

The procedure of Example 1 is followed substituting 0.6 to 0.8 mm plates for the extruder plates.

The carbonic anhydrase inhibitor active medicament release rate of the active spherical granules is determined by U.S.P. XXI test methods stirring with paddles in a medium with a pH of 4.5 and an acetate buffer. The results are summarized in Table III and appear in FIG. 4 in graph form.

EXAMPLE 7

The procedure of Example 1 is followed substituting plates with openings of less than 0.6 mm for the extruder plates.

The carbonic anhydrase inhibitor active medicament release rate of the active spherical granules is determined by U.S.P. XXI test methods stirring with paddles in a medium with a pH of 4.5 and an acetate buffer. The results are summarized in Table III and appear in FIG. 4 in graph form.

TABLE III

Effect of Sphere Size on Carbonic Anhydrase Inhibitor Active Medicament[A] Release Rate from Active Spherical Granules

| Time Minutes | 1.2–1.8 mm (Example 5) Percent Released[B] | 0.8–1.2 mm (Example 1) Percent Released[B] | 0.6–0.8 mm (Example 6) Percent Released[B] | 0.6 mm (Example 7) Percent Released[B] |
|---|---|---|---|---|
| 30  | 15.60 ± 0.0  | 14.8 ± 0.8 | 17.15 ± 0.35 | 21.73 ± 1.19 |
| 60  | 23.80 ± 0.28 | 22.6 ± 0.5 | 25.45 ± 0.64 | 32.50 ± 1.15 |
| 120 | 34.35 ± 0.07 | 33.3 ± 0.5 | 36.70 ± 0.42 | 46.03 ± 1.31 |
| 180 | 41.90 ± 0.14 | 41.3 ± 0.4 | 45.10 ± 0.71 | 55.40 ± 0.85 |
| 240 | 48.00 ± 0.28 | 47.6 ± 0.5 | 51.90 ± 0.71 | 62.57 ± 0.67 |
| 300 | 53.20 ± 0.42 | 53.0 ± 0.6 | 57.50 ± 0.85 | 68.47 ± 0.49 |
| 360 | 57.55 ± 0.92 | 57.8 ± 0.5 | 62.35 ± 0.78 | 73.30 ± 0.60 |
| 480 | 65.10 ± 0.14 | 65.5 ± 0.4 | 70.90 ± 1.13 | 80.43 ± 0.93 |
| 600 | 71.45 ± 0.35 | 72.2 ± 0.5 | 78.30 ± 0.85 | 86.07 ± 1.12 |
| 660 | 74.75 ± 0.49 | 75.5 ± 0.5 | 81.65 ± 1.06 | 88.57 ± 1.29 |
| 720 | 77.45 ± 0.21 | 78.2 ± 0.5 | 84.55 ± 0.92 | 90.63 ± 1.31 |

A—methazolamide - Neptazane ® - Lederle Laboratories
B—U.S.P. XXI test method; medium pH 4.5 with acetate buffer; stirred with paddles.

Examples 1 and 5–7 indicate that carbonic anhydrase inhibitor active medicament containing active spherical granule diameters can be manipulated to enhance controlled release rates.

EXAMPLE 8

A soft shell capsule is filled with active spherical granules prepared by the method of Example 1 to produce a soft shell capsule oral dosage unit form having a label potency of 50 mg of carbonic anhydrase inhibitor active medicament.

Figure 5:
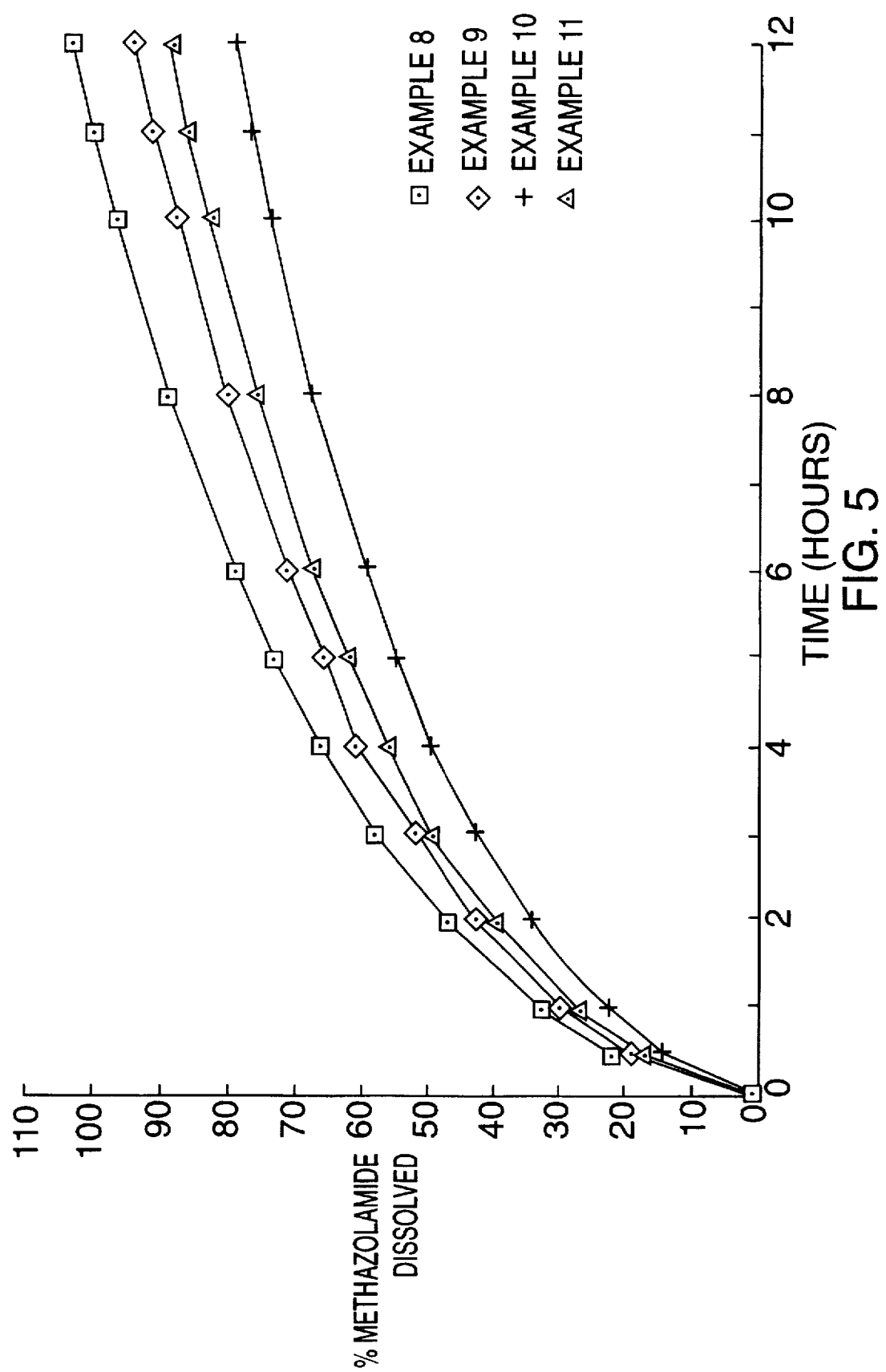
FIG. 5 is a graphic illustration of the release rate of carbonic anhydrase inhibitor active medicament from hard and from soft shell capsules filled with active spherical granules containing carbonic anhydrase inhibitor active medicament according to the present invention.

The carbonic anhydrase inhibitor active medicament release rate of the capsule is determined by U.S.P. XXI test methods stirring with paddles in a medium with a pH of 4.5 and an acetate buffer. The results appear in FIG. 5 in graph form.

EXAMPLE 9

A hard shell capsule is filled with active spherical granules prepared by the method of Example 1 to produce a hard shell capsule oral dosage unit form having a label potency of 50 mg of carbonic anhydrase inhibitor active medicament.

The carbonic anhydrase inhibitor active medicament release rate of the capsule is determined by U.S.P. XXI test methods stirring with paddles in a medium with a pH of 4.5 and an acetate buffer. The results appear in FIG. 5 in graph form.

EXAMPLE 10

A blend is prepared by mixing 75 parts of carbonic anhydrase inhibitor active medicament, methazolamide (Neptazane®—Lederle Laboratories), and 25 parts of normally solid diluent adaptable to form a diffusable matrix for the carbonic anhydrase inhibitor active medicament, microcrystalline cellulose (Avicel®—PH-101—FMC Corp.), in a planetary mixer for 10 minutes. The blend is then granulated to an extrudable consistency with the addition of water, and the resultant granulate is extruded through a 1.0 mm plate. The resultant extrudate is spheronzied at high speed for one or two minutes. The resultant spherical granules are dried in a fluid bed dryer at 65° C. to 70° C. until the moisture content is about 2.54 percent to form active spherical granules.

A soft shell capsule is filled with the active spherical granules to produce a soft shell capsule oral dosage unit form having a label potency of 50 mg of carbonic anhydrase inhibitor active medicament.

The carbonic anhydrase inhibitor active medicament release rate of the capsule is determined by U.S.P. XXI test methods stirring with paddles in a medium with a pH of 4.5 of an acetate buffer. The results appear in FIG. 5 in graph form.

EXAMPLE 11

A blend is prepared by mixing 75 parts of carbonic anhydrase inhibitor active medicament, methazolamide (Neptazane®—Lederle Laboratories), and 25 parts of normally solid diluent adaptable to form a diffusable matrix for the carbonic anhydrase inhibitor active medicament, microcrystalline cellulose (Avicel®—PH-101—FMC Corp.), in a planetary mixer for 10 minutes. The blend is then granulated to an extrudable consistency with the addition of water, and the resultant granulate is extruded through a 1.0 mm plate. The resultant extrudate is spheronzied at high speed for one or two minutes. The resultant spherical granules are dried in a fluid bed dryer at 65° C. to 70° C. until the moisture content is about 2.54 percent, to form active spherical granules.

A hard shell capsule is filled with active spherical granules to produce a hard shell capsule oral dosage unit form having a label potency of 50 mg of carbonic anhydrase inhibitor active medicament.

The carbonic anhydrase inhibitor active medicament release rate of the capsule is determined by U.S.P. XXI test methods stirring with paddles in a medium with a pH of 4.5 and an acetate buffer. The results appear in FIG. 5 in graph form.

Example 8 when compared with Example 9 and Example 10 when compared with Example 11 demonstrate that the type of capsule, i.e. hard or soft, has only a small effect on the controlled release properties of capsule oral dosage unit forms of the present invention.

Examples 8 and 9 when compared with Example 1 demonstrate how the controlled release properties of carbonic anhydrase inhibitor active medicament containing active spherical granules are enhanced when filled into hard or soft shell capsules.

EXAMPLE 12

A blend is prepared by mixing 10 parts of carbonic anhydrase inhibitor active medicament, methazolamide (Neptazane®—Lederle Laboratories), and 90 parts of normally solid diluent adaptable to form a diffusable matrix for the carbonic anhydrase inhibitor active medicament, microcrystalline cellulose (Avicel®—PH-101—FMC Corp.), in a planetary mixer for 10 minutes. The blend is then granulated to an extrudable consistency with the addition of water, and the resultant granulate is extruded through a 1.0 mm plate. The resultant extrudate is spheronized at high speed for one to three minutes. The resultant spherical granules are dried in a fluid bed dryer at 65° C. to 70° C. until the moisture content is about 2.54 percent, to form active spherical granules.

Figure 6:
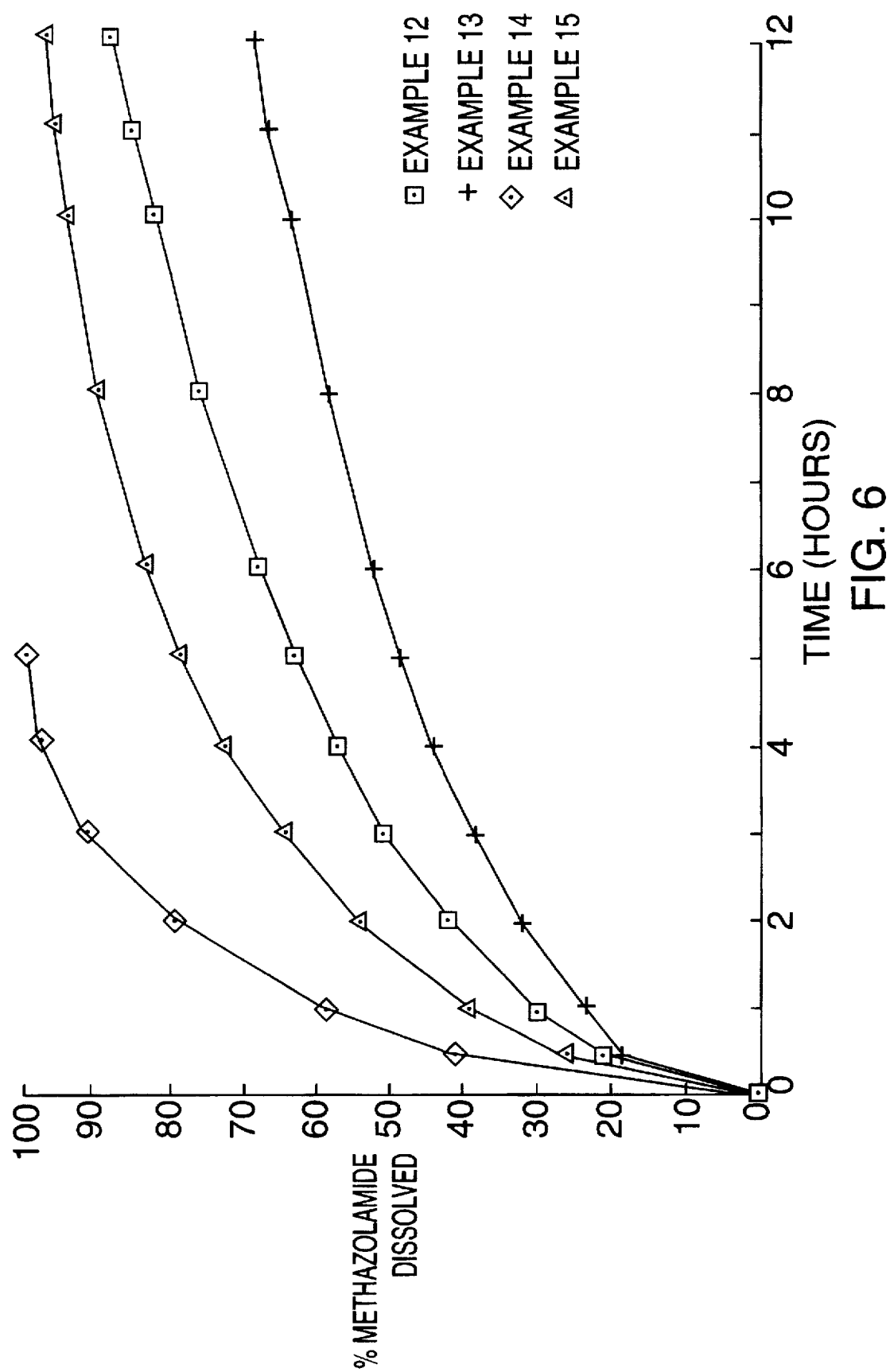
FIG. 6 is a graphic illustration of the effect of optional excipients on the release rate of carbonic anhydrase inhibitor active medicament from active spherical granules of the present invention.

The carbonic anhydrase inhibitor active medicament release rate of the active spherical granules is determined by U.S.P. XXI test methods stirring with paddles in a medium with a pH of 4.5 and an acetate buffer. The results appear in FIG. 6 in graph form.

EXAMPLE 13

A blend is prepared by mixing 25 parts of carbonic anhydrase inhibitor active medicament, methazolamide (Neptazane®—Lederle Laboratories), and 75 parts of normally solid diluent adaptable to form a diffusable matrix for the carbonic anhydrase inhibitor active medicament, microcrystalline cellulose (Avicel®—PH-101— FMC Corp.), in a planetary mixer for 10 minutes. The blend is then granulated to an extrudable consistency with the addition of water, and the resultant granulate is extruded through a 1.0 mm plate. The resultant extrudate is spheronized at high speed for one to three minutes. The resultant spherical granules are dried in a fluid bed dryer at 65° C. to 70° C. until the moisture content is about 2.54 percent, to form active spherical granules.

The carbonic anhydrase inhibitor active medicament release rate of the active spherical granules is determined by U.S.P. XXI test methods stirring with paddles in a medium with a pH of 4.5 and an acetate buffer. The results appear in FIG. 6 in graph form.

EXAMPLE 14

A blend is prepared by mixing 10 parts of carbonic anhydrase inhibitor active medicament, methazolamide (Neptazane®—Lederle Laboratories), 50 parts of normally solid diluent adaptable to form a diffusable matrix for the carbonic anhydrase inhibitor active medicament, microcrystalline cellulose (Avicel®—PH-101—FMC Corp.), and 40 parts of excipient, lactose, in a planetary mixer for 10 minutes. The blend is then granulated to an extrudable consistency with the addition of water, and the resultant granulate is extruded through a 1.0 mm plate. The resultant extrudate is spheronized at high speed for one to three minutes. The resultant spherical granules are dried in a fluid bed dryer at 65° C. to 70° C. until the moisture content is about 2.54 percent, to form active spherical granules.

The carbonic anhydrase inhibitor active medicament release rate of the active spherical granules is determined by U.S.P. XXI test methods stirring with paddles in a medium with a pH of 4.5 and an acetate buffer. The results appear in FIG. 6 in graph form.

EXAMPLE 15

A blend is prepared by mixing 25 parts of carbonic anhydrase inhibitor active medicament, methazolamide (Neptazane®—Lederle Laboratories), 50 parts of normally solid diluent adaptable to form a diffusable matrix for the carbonic anhydrase inhibitor active medicament, microcrystalline cellulose (Avicel®—PH-101—FMC Corp.), and 25 parts of excipient, lactose, in a planetary mixer for 10 minutes. The blend is then granulated to an extrudable consistency with the addition of water, and the resultant granulate is extruded through a 1.0 mm plate. The resultant extrudate is spheronized at high speed for one to three minutes. The resultant spherical granules are dried in a fluid bed dryer at 65° C. to 70° C. until the moisture content is about 2.54 percent, to form active spherical granules.

The carbonic anhydrase inhibitor active medicament release rate of the active spherical granules is determined by U.S.P. XXI test methods stirring with paddles in a medium with a pH of 4.5 and an acetate buffer. The results appear in FIG. 6 in graph form.

Example 14 when compared with Example 12 and Example 15 when compared with Example 13 demonstrate the effect that the addition of the optional pharmaceutically acceptable excipient may have on the controlled release properties of carbonic anhydrase inhibitor active medicament containing active spherical granules. Release rates are generally accelerated by the addition of excipient to the active spherical granules.

The above-mentioned patents, publications and test methods are incorporated herein by reference.

Many variations will suggest themselves to those skilled in this art in light of the foregoing detailed description. The carbonic anhydrase inhibitor active medicament may comprise acetazolamide. As a film former, ethyl cellulose can be used alone. All such obvious variations are within the full intended scope of the appended claims.

We claim:

1. A controlled release pharmaceutical composition in oral dosage unit form comprising a hard or a soft shell capsule containing a filling comprising
   (A) a therapeutically effective number of active spherical granules comprising
      (i) an effective amount of a carbonic anhydrase inhibitor active medicament selected from the group consisting of acetazolamide and methazolamide;
      (ii) a pharmaceutically acceptable normally solid diluent adapted to form a diffusable matrix for said at least one carbonic anhydrase inhibitor active medicament (A)(i); and, optionally,
      (iii) at least one pharmaceutically acceptable excipient which may be the same as or different than (A)(ii).

2. An oral dosage unit as defined in claim 1 wherein said carbonic anhydrase inhibitor active medicament (A)(i) comprises from about 10 to about 90 parts by weight, said normally solid diluent adapted to form a diffusable matrix for said at least one carbonic anhydrase inhibitor active medicament (A)(i), (A)(ii) comprises from about 90 to about 10 parts by weight and said excipient (A)(iii) comprises from zero to about 75 parts by weight based upon 100 parts by weight of said active spherical granules (A).

3. An oral dosage unit as defined in claim 2 wherein said carbonic anhydrase inhibitor active medicament (A)(i) comprises from about 10 to about 80 parts by weight, said normally solid diluent adapted to form a diffusable matrix for said at least one carbonic anhydrase inhibitor active medicament (A)(i), (A)(ii) comprises from about 75 to about 10 parts by weight, and said excipient (A)(iii) comprises from about 10 to about 75 parts by weight based upon 100 parts by weight of said active spherical granules (A).

4. An oral dosage unit as defined in claim 3 wherein said carbonic anydrase inhibitor active medicament (A)(i) comprises about 25 parts by weight, said normally solid diluent adapted to form a diffusable matrix for said at least one carbonic anhydrase inhibitor active medicament (A)(i). (A)(ii) comprises from about 25 parts to about 65 parts by weight and said excipient (A)(iii) comprises from about 10 to about 50 parts by weight based upon 100 parts by weight of said active spherical granules (A).

5. An oral dosage unit as defined in claim 2 wherein said carbonic anhydrase inhibitor active medicament (A)(i) comprises from about 10 to about 75 parts by weight and said normally solid diluent adapted to form a diffusable matrix for said at least one carbonic anhydrase inhibitor active medicament (A)(i), (A)(ii) comprises from about 90 to about 25 parts by weight based upon 100 parts by weight of said active spherical granules (A).

6. An oral dosage unit as defined in claim 5 wherein said carbonic anhydrase inhibitor active medicament (A)(i) comprises about 50 parts by weight and said normally solid diluent adapted to form a diffusable matrix for said at least one carbonic anhydrase inhibitor active medicament (A)(i), (A)(ii) comprises about 50 parts by weight based upon 100 parts by weight of said active spherical granules (A).

7. An oral dosage unit as defined in claim 1 containing from about 25 mg to about 75 mg of methazolamide.

8. An oral dosage unit as defined in claim 7 wherein not more than about 50 percent of said methazolamide is released from said active spherical granules (A) in about one hour and not less than about 75 percent of said methazolamide is released from said active spherical granules in about 12 hours when suspended in pH 4.5 acetate buffer at about 37° C. at a methazolamide concentration of about 50 mg of methazolamide/900 ml of buffer.

9. An oral dosage unit as defined in claim 1 wherein said normally solid diluent adapted to form a diffusable matrix (A)(ii) comprises microcrystalline cellulose.

10. An oral dosage unit as defined in claim 1 wherein said pharmaceutically acceptable excipient (A)(iii) comprises microcrystalline cellulose, polyvinylpyrrolidone, hydroxypropylmethyl cellulose, microcrystalline cellulose in combination with lactose, microcrystalline cellulose in combination with sodium carboxymethyl cellulose or a mixture of any of the foregoing.

11. An oral dosage unit as defined in claim 1 wherein said active spherical granules (A) have an average diameter in the range of from about 0.1 to about 2.5 millimeters.

12. An oral dosage unit as defined in claim 11 wherein said active spherical granules (A) have an average diameter in the range of from about 0.8 to about 1.2 millimeters.

13. An oral dosage unit as defined in claim 1 wherein said active spherical granules (A) include a layer of a polymer coating.

14. An oral dosage unit as defined in claim 13 wherein said polymer comprises from about 1 to less than about 25 parts by weight based upon 100 parts by weight of (A).

15. An oral dosage unit as defined in claim 14 wherein said polymer comprises from about 1 to about 5 percent by weight based upon 100 parts by weight of (A).

16. An oral dosage unit as defined in claim 14 wherein said polymer is selected from (a) methylcellulose;
(b) ethylcellulose;
(c) hydroxyethyl cellulose;
(d) hydroxypropyl cellulose;
(e) hydroxypropyl methylcellulose;
(f) hydroxypropyl methylcellulose phthalate;
(g) cellulose acetate phthalate;
(h) hydroxypropyl methylcellulose succinate;
(i) a polymer or copolymer of (meth)acrylic acid or an ester thereof; or
(j) a mixture of any of the foregoing, alone, or in further combination with a plasticizer, a colorant or a pigment.

17. An oral dosage unit as defined in claim 1 which also includes a top layer of the same or a different polymer over an intermediate polymer layer.

18. An oral dosage unit as defined in claim 17 wherein said intermediate layer and said top layer comprise hydroxypropyl methylcellulose.

19. An oral dosage unit as defined in claim 1 wherein said therapeutically effective number of active spherical granules (A) comprise a mixture of (A-1) a therapeutically effective number of active spherical granules comprising (i) an effective amount of at least one carbonic anhydrase inhibitor selected from the group consisting of acetazolamide and methazolamide;
(ii) a pharmaceutically acceptable normally solid diluent adapted to form a diffusable matrix for said at least one carbonic anhydrase inhibitor active medicament (A-1)(i); and, optionally,
(iii) at least one pharmaceutically acceptable excipient which may be the same as or different than (A-1)(ii); and (A-2) a therapeutically effective number of active spherical granules comprising (i) an effective amount of at least one active medicament which is different than (A-1)(i);
(ii) a pharmaceutically acceptable normally solid diluent adapted to form a diffusable matrix for said at least one active medicament (A-2)(i) which is the same as or different than (A-1)(ii); and, optionally,
(iii) at least one pharmaceutically acceptable excipient which may be the same as or different than (A-1)(ii).

20. An oral dosage unit as defined in claim 1 which also includes (B) a lubricant;
(C) a disintegrant;
(D) a plasticizer;
(E) a colorant;
(F) a pigment;
(G) a flavoring;
(H) an active medicament which is the same as or different than with (A)(i); or
(I) a combination of any of the foregoing.

21. A method of controlling the release of at least one carbonic anhydrase inhibitor active medicament in the blood stream of a warm-blooded mammal over a prolonged period of time comprising the ingestion of an oral dosage unit as defined in claim 1.

22. A method for the preparation of a controlled release pharmaceutical composition in oral dosage unit form comprising a hard or a soft shell capsule containing a filling, comprising the steps of:

(a) blending
(i) an effective amount of a carbonic anhydrase inhibitor active medicament selected from the group consisting of acetazolamide and methazolamide;
(ii) a pharmaceutically acceptable normally solid diluent adaptable to form a diffusable matrix for said at least one carbonic anhydrase inhibitor active medicament (a)(i); and optionally,
(iii) at least one pharmaceutically acceptable excipient which may be the same as or different than (a)(ii);
(b) granulating the resultant, blend of step (a) in the presence of a granulating liquid;
(c) extruding the resultant granulate of step (b);
(d) spheronizing the resultant extrudate of step (c) to form active spherical granules (A) derived from step (a);
(e) drying active spherical granules (A);
(f) at least partially filling a hard shell or a soft shell capsule with a therapeutically effective number of active spherical granules, (A); and optionally,
(g) sealing said capsule.

23. A method as defined in claim 22 wherein said granulating liquid in step (b) comprises water in an amount sufficient to provide excessive wetting of said blend of step (a).

24. A controlled release pharmaceutical composition in oral dosage unit form comprising a hard or a soft shell capsule containing a filling comprising (A) a therapeutically effective number of active spherical granules comprising
 (i) a total of from about 25 mg to about 75 mg of methazolamide;
 (ii) microcrystalline cellulose adapted with water, the amount of water used for said adaptation being greater than 30 percent by weight of microcrystalline cellulose and water combined, to form a diffusable matrix for said methazolamide; and, optionally,
 (iii) lactose.

25. An oral dosage unit as defined in claim 1 wherein the carbonic anhydrase inhibitor is acetazolamide.

26. An oral dosage unit as defined in claim 1 wherein the carbonic anhydrase inhibitor is methazolamide.

27. A controlled release pharmaceutical composition in oral dosage unit form comprising a hard or a soft shell capsule containing a filling which consists essentially of:

(A) a therapeutically effective number of active spherical granules comprising
 (i) an effective amount of a carbonic anhydrase inhibitor active medicament selected from the group consisting of acetazolamide and methazolamide;
 (ii) a pharmaceutically acceptable normally solid diluent adapted to form a diffusable matrix for said at least one carbonic anhydrase inhibitor active medicament (A)(i); and, optionally,
 (iii) at least one pharmaceutically acceptable excipient which may be the same as or different than (A)(ii).

\* \* \* \* \*